United States Patent [19]
Ferree et al.

[11] Patent Number: 4,576,034
[45] Date of Patent: Mar. 18, 1986

[54] ADJUSTABLE RADIUS APPARATUS FOR CALIBRATING ULTRASONIC TRANSDUCER ARRAY

[75] Inventors: Herbert E. Ferree, Hempfield Twp.; Daniel E. Klinvex, McKeesport; Robert P. Vestovich, Monroeville, all of Pa.

[73] Assignee: Westinghouse Electric Corp., Pittsburgh, Pa.

[21] Appl. No.: 584,226

[22] Filed: Feb. 27, 1984

[51] Int. Cl.⁴ ............................................. G01C 25/00
[52] U.S. Cl. ..................................... 73/1 DV; 367/13
[58] Field of Search ........................ 73/1 DV; 367/13

[56] References Cited

U.S. PATENT DOCUMENTS

| | | | |
|---|---|---|---|
| 3,248,933 | 5/1966 | Stebbins | 73/71.5 |
| 3,480,002 | 11/1969 | Flaherty et al. | 128/2 |
| 3,678,736 | 7/1972 | May | 73/67.85 |
| 3,765,229 | 10/1973 | Spencer et al. | 73/67.85 |
| 3,894,425 | 7/1975 | Winters et al. | 73/67.85 |
| 3,952,581 | 4/1976 | Gottelt | 73/67.85 |
| 3,990,300 | 11/1976 | Kossoff | 73/67.85 |
| 4,117,733 | 10/1978 | Gugel | 73/634 |
| 4,385,523 | 5/1983 | Gugel et al. | 73/640 |

FOREIGN PATENT DOCUMENTS 2547472 4/1977 Fed. Rep. of Germany .
55-42022 3/1980 Japan .

OTHER PUBLICATIONS

"Setup for Ultrasonic Inspection of Welded Joints in Annular Blanks," *Soviet Journal of Nondes. Testing*, vol. 10, No. 3, pp. 356-358 (May-Jun., 1974).

*Primary Examiner*—Peter Chin
*Attorney, Agent, or Firm*—L. A. DePaul

[57] ABSTRACT

Calibration apparatus for calibrating an ultrasonic transducer array by moving it along an arcuate calibration test member, includes four upright posts interconnected by a rectangular carriage which is slidably movable vertically along the posts. A horizontal pivot shaft is rotatably mounted on the carriage. Fixed to the shaft and depending therefrom are two pendulum arms, interconnected at their lower ends by a pair of cross bars on which is slidably mounted a mounting block. An attachment rod is vertically slidably movable in the mounting block and carries a coupling joint at its lower end for mounting the transducer array. A reversible gearmotor drives the pivot shaft through a chain and sprocket assembly in an oscillating motion. Backlash in the gear train is reduced by a bias weight.

15 Claims, 5 Drawing Figures

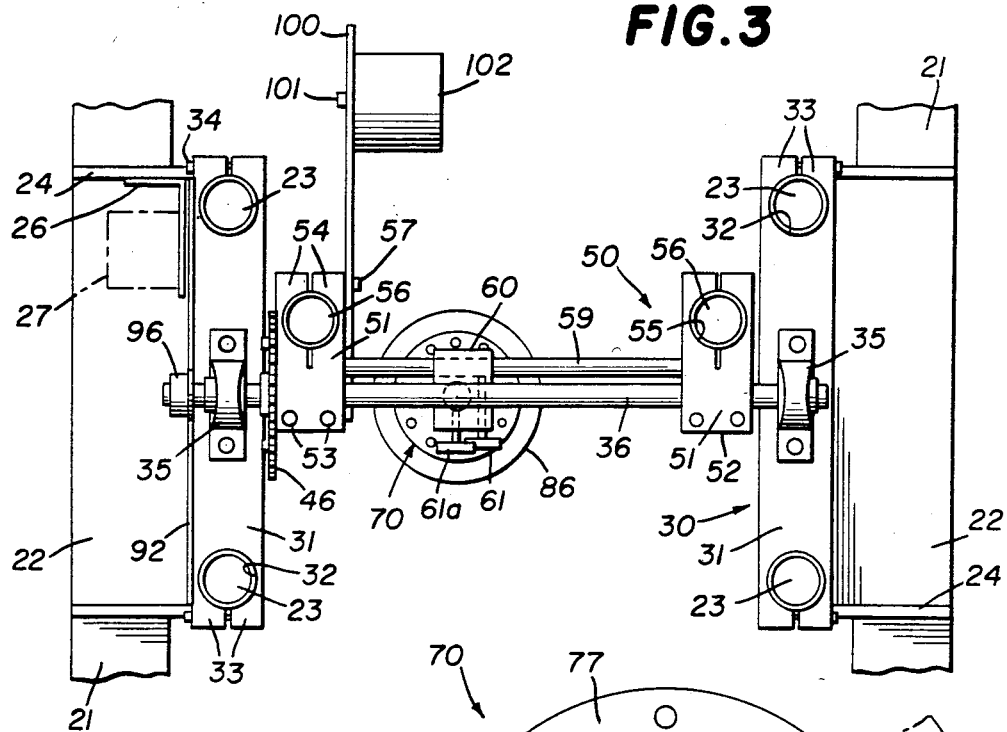
FIG. 3
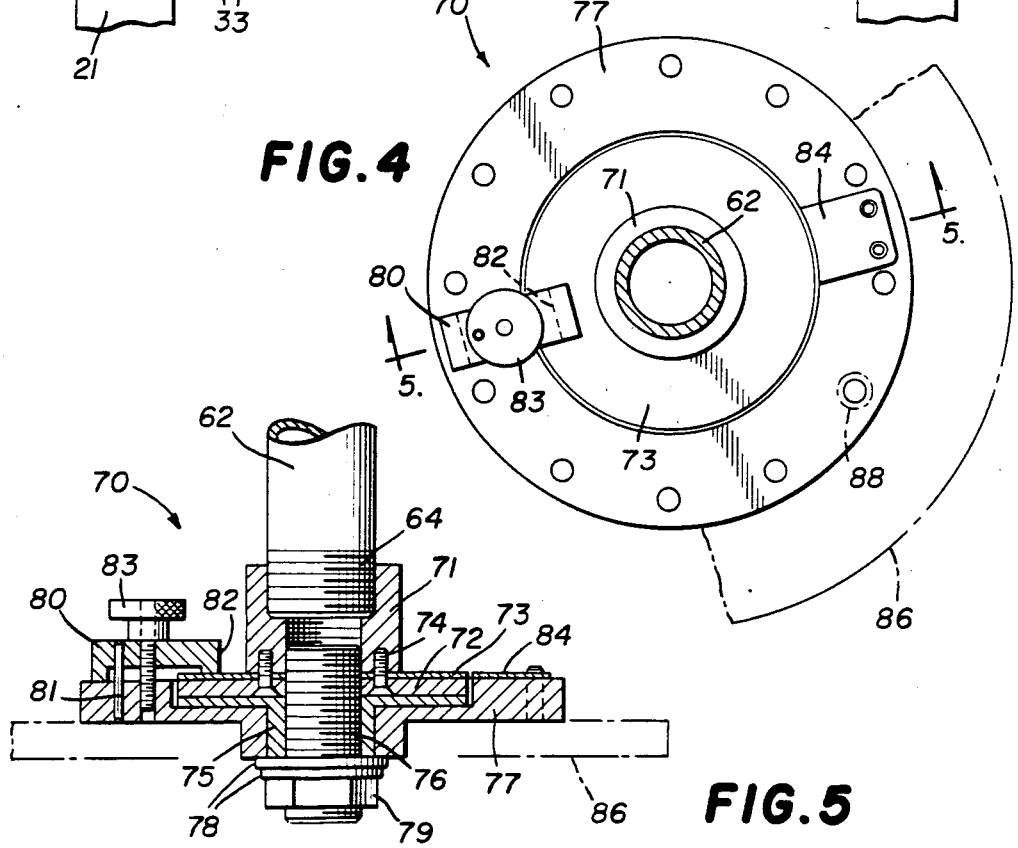
FIG. 4
FIG. 5

ADJUSTABLE RADIUS APPARATUS FOR CALIBRATING ULTRASONIC TRANSDUCER ARRAY

BACKGROUND OF THE INVENTION

The present invention relates to calibration apparatus for calibrating ultrasonic transducer arrays. In particular, the invention relates to the calibration of transducer arrays which are intended for the inspection of curved surfaces of varying radii, such as the surfaces of the reactor and steam generator vessels in a nuclear steam generating plant during in-service inspection of the plant.

In nuclear steam generating plants, it is necessary to periodically inspect the interior of the reactor as well as the steam generating vessel for structural flaws. For this purpose, an ultrasonic transducer array having a plurality of transmitting and receiving transducers arranged at different angles are carried by a manipulating tool and moved along the surface to be inspected, a predetermined distance therefrom. In order to insure accurate readings from the ultrasonic transducer array, it is necessary that it be periodically calibrated for a particular surface which is to be inspected. This calibration cannot be effected when the transducer array is mounted on the manipulator tool, because the manipulator tool is an extremely expensive device which is in constant use. Therefore, calibration of the transducer array must be effected remotely before the array is mounted on the manipulator tool.

For this purpose, calibration test blocks are provided which have surfaces which duplicate the surfaces of the reactor which are to be inspected. The transducer array is mounted in a calibration fixture which moves the distance therefrom. Because the test surface is curved, complicated cam follower mechanisms with curved templates have previously been used for controlling the movement of the transducer array along the test block. However, this requires an inordinately large number of expensive templates, because of the variety of surfaces to be inspected and the variety of distances from the surface at which the transducer array must be maintained because of different water levels in the reactor.

Pendulum-type manipulators have been utilized in ultrasonic inspection systems for controlling the movement of the transducer array during the inspection operation. But such manipulators have not heretofore been used in a calibration fixture. Furthermore, the pendulum-type manipulators used heretofore have been relatively unstable and would not be suitable for the heavy duty use in a nuclear reactor and would not provide the desired accuracy. Furthermore, such pendulum devices have not been suitable for use with surfaces of varying radii. While pendulums with extensible arms are known, this type of adjustment would require movement of the surface being inspected with respect to the pendulum frame, or vice versa, in order to maintain the proper spacing between the transducer array and the surface being inspected. Furthermore, prior pendulum-type devices could not readily be stopped and retained at any position of the pendulum arc without the use of special locking or retaining means.

SUMMARY OF THE INVENTION

It is a general object of the present invention to provide an improved calibration apparatus which avoids the disadvantages of prior apparatuses while affording additional structural and operating advantages.

An important object of the invention is the provision of a calibration apparatus which is of simple and economical construction.

In connection with the foregoing object, it is another object of this invention to provide a calibration apparatus of the type set forth, which is rugged, stable and accurate.

In connection with the foregoing objects, still another object of the invention is the provision of a calibration apparatus which utilizes a pendulum motion wherein the position of the pivot axis of the pendulum is variable.

In connection with the foregoing object, yet another object of the invention is the provision of a calibration apparatus of the type set forth, in which the pendulum can be stopped and stably maintained at any position along its swinging arc, without the use of special retaining means.

These and other objects of the invention are attained by providing calibration apparatus for calibrating an ultrasonic transducer array by moving it along an arcuate calibration test member, the apparatus comprising: a frame disposable adjacent to the test member, carriage means mounted on the frame and defining a pivot axis extending through the center of curvature of the test member, means for changing the position of the carriage means on the frame for varying the position of the pivot axis with respect to the test member thereby to accommodate test members with different radii of curvature, an elongated pendulum arm mounted on the carriage and depending therefrom for pivotal movement about the pivot axis, drive means for effecting pivotal movement of the pendulum arm, and attachment means for mounting the transducer array on the lower end of the pendulum arm, whereby pivoting of the pendulum arm effects movement of the transducer array along the arcuate test member at a fixed predetermined distance therefrom.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 3 is a fragmentary top plan view of the apparatus of FIG. 2, but on the same scale as FIG. 1;

FIG. 4 is an enlarged top plan view of the transducer mounting assembly of the present invention; and FIG. 5 is a view in vertical section taken along the line 5—5 in FIG. 4.

DESCRIPTION OF THE PREFERRED EMBODIMENT

Figure 1:
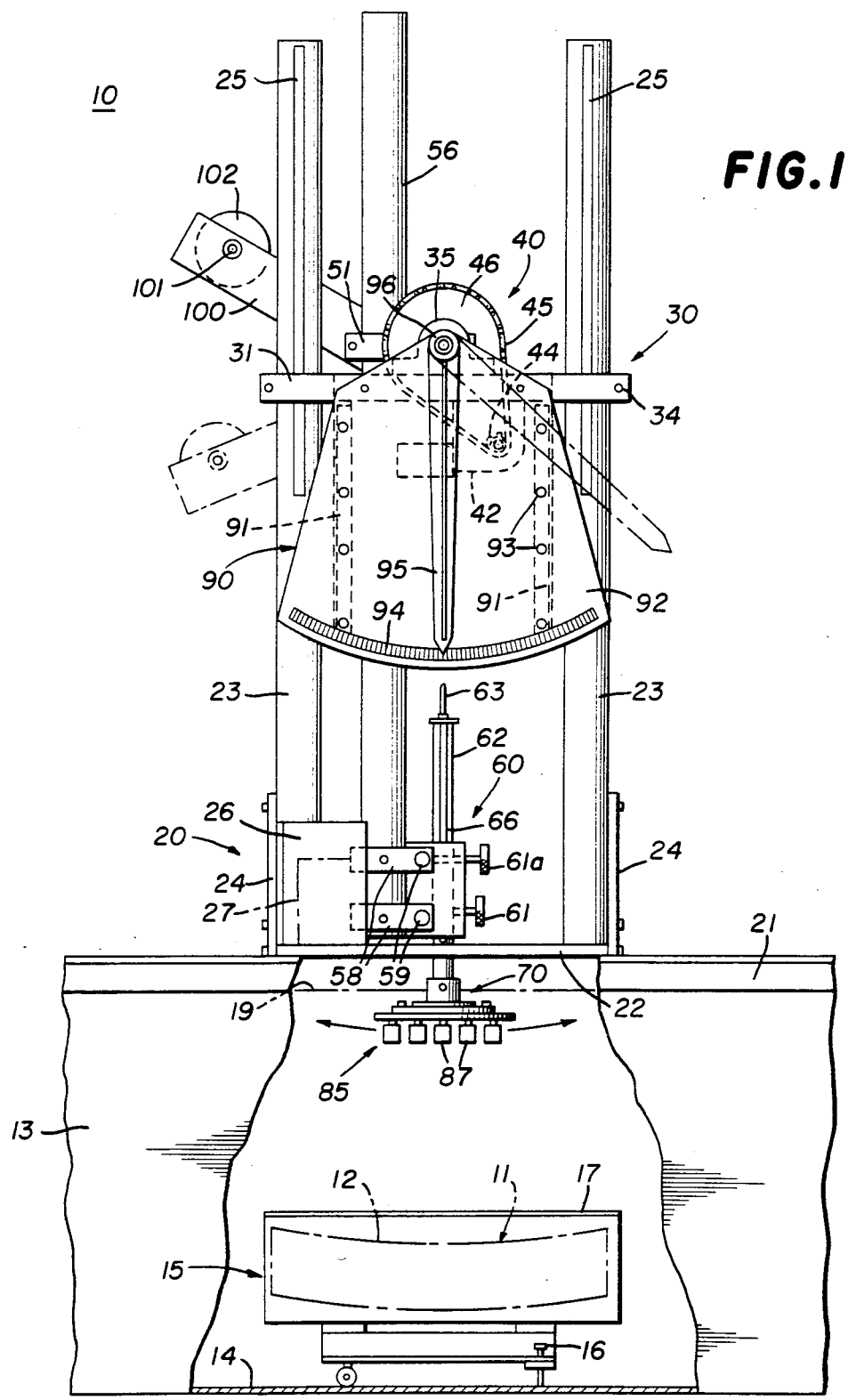
FIG. 1 is a fragmentary front elevational view of a calibration apparatus constructed in accordance with and embodying the features of the present invention, shown mounted on a calibration tank with portions broken away more clearly to show the construction.
Figure 2:
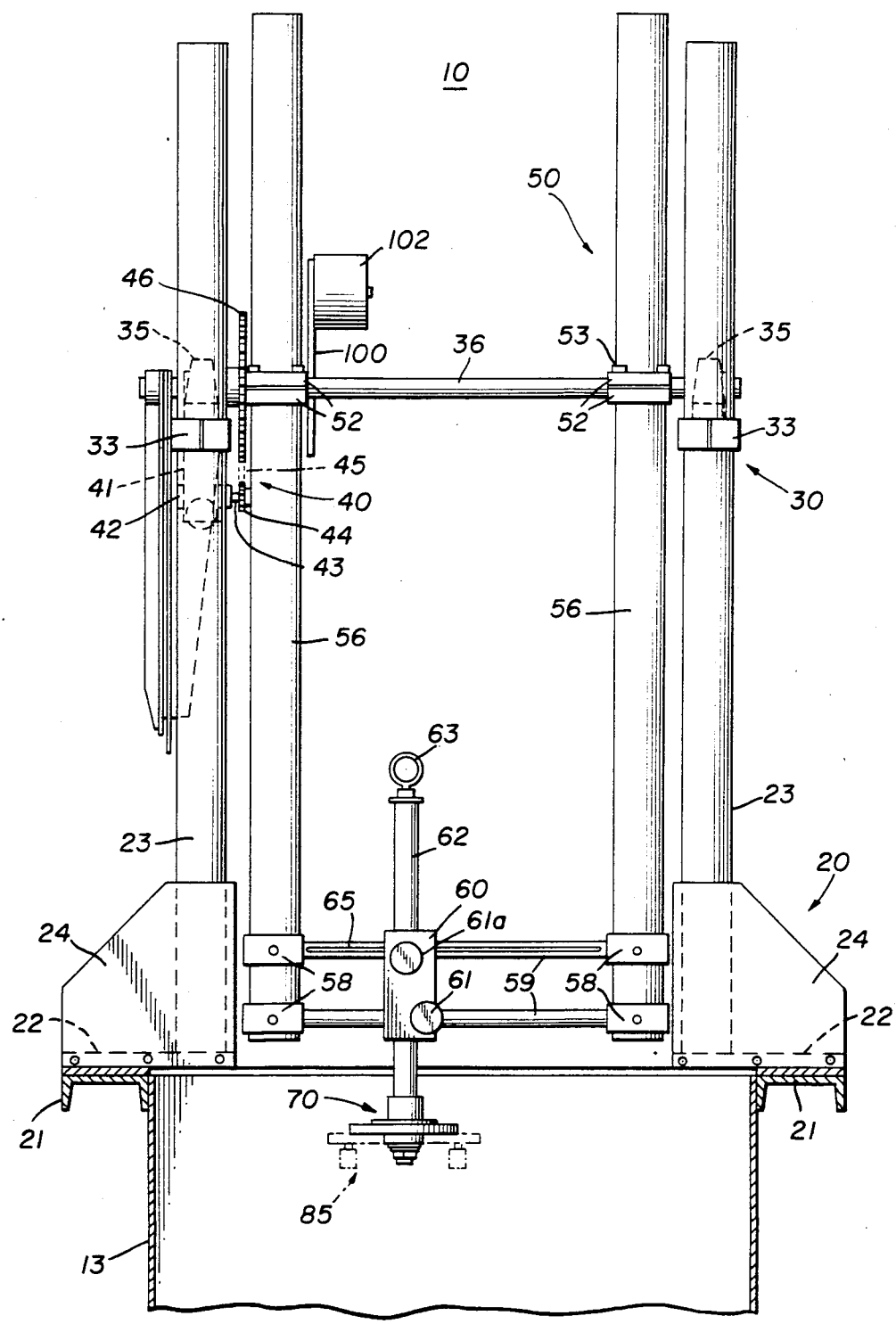
FIG. 2 is a slightly enlarged side elevational view of the apparatus of FIG. 1, as viewed from the righthand side thereof, with the calibration tank in vertical section.

Referring to FIGS. 1-3 of the drawings, there is illustrated a calibration apparatus, generally designated by the numeral 10 for calibrating a transducer array 85. The transducer array 85 is calibrated by moving it across a calibration block 11 which has an arcuate upper surface 12 identical in curvature to a portion of a nuclear steam generating vessel to be inspected by the transducer array as part of an ultrasonic inspection process. The calibration block 11 is immersed in water in a calibration tank 13, and more particularly, is supported on the floor 14 thereof. The water provides a transmission medium for the ultrasonic waves. The calibration block 11 may be supported in an underwater load bearing device 15 which has a frame 16 carrying a support box 17 in which the calibration block 11 is mounted. The tank 13 is filled with water to a level 19. The calibration block 11 has known defects so that the response of the transducer array 85 thereto can form a basis for calibration.

The calibration apparatus 10 includes a support frame 20 which is mounted on top of the calibration tank 13. The support frame 20 includes a pair of channel beams 21 extending alongside the tank 13 and fixedly secured thereto adjacent to the upper end thereof. Mounted on the channel beams 21 are two rectangular support plates 22, respectively disposed along opposite sides of the tank 13. Each support plate 22 carries a pair of support posts 23 which are fixedly secured to the support plate 22 and extend vertically upwardly therefrom. Four gusset plates 24 are respectively associated with the support posts 23, each gusset plate 24 interconnecting the associated support post 23 and the adjacent end of the associated support plate 22. Each of the support posts 23 of one pair thereof has formed on the outer surface thereof, facing outwardly toward one side of the tank 13, an elongated linear scale 25. The support plate 22 carrying those support posts 23 also has mounted thereon a mounting bracket 26 on which is supported an associated control box 27 for controlling the operation of the calibration apparatus 10.

The four support posts 23 are identical in construction, each being in the form of a circular cylinder, the posts 23 being arranged in a rectangular configuration. Mounted on the support posts 23 is a pendulum carriage assembly, generally designated by the numeral 30. More particularly, two horizontally extending clamp bars 31 are provided, each clamp bar 31 interconnecting an associated pair of the support posts 23. Each clamp bar 31 has cylindrical vertical bores 32 therethrough adjacent to the opposite ends thereof for respectively receiving the associated support posts 23, each end of the clamp bar 31 being formed with a pair of vertically-split ends 33 secured together by a clamp bolt 34 securely to clamp the clamp bar 31 to the support posts 23. Two pillow blocks 35 are respectively carried by the clamp bars 31 intermediate the ends thereof and projecting upwardly therefrom. An elongated shaft 36 spans the clamp bars 31 substantially perpendicular thereto and has the opposite ends thereof respectively journaled in bearings of the pillow blocks 35. It will be appreciated that by loosening the bolts 34, the pendulum carriage assembly may be moved vertically along the support posts 23 to any desired position, the accurate location of such position being facilitated by the linear scales 25.

Mounted on the pendulum carriage assembly 30 is a drive assembly 40 which includes a mounting bracket 41 carried by one of the clamp bars 31 and on which is mounted a gearmotor 42 including a high ratio speed-reduction gear train. The gearmotor 42 has an output shaft 43 to which is fixedly secured a sprocket 44, which is in turn coupled by a drive chain 45 to a sprocket 46 fixedly secured to the shaft 36. The gearmotor 42 is reversible, and it will be appreciated that rotation of the output shaft 43 effects a corresponding rotation of the shaft 36.

Carried by the shaft 36 is a pendulum assembly 50 which includes a pair of clamp blocks 51, respectively having bores therethrough for receiving the shaft 36, and provided with horizontally split ends 52 secured together by fasteners 53 securely to clamp the clamp blocks 51 to the shaft 36. Each of the clamp blocks 51 projects rearwardly from the shaft 36 and is provided adjacent to its rearward end with a vertical bore 55 for receiving a corresponding one of two elongated cylindrical pendulum arms 56. Each of the clamp blocks 51 has vertically split rear ends 54 which are secured together by fasteners 57 securely to clamp the clamp blocks 51 to the pendulum arms 56. Each of the pendulum arms 56 has a length approximately the same as that of the support posts 23 and extends substantially parallel thereto.

Each of the pendulum arms 56 has fixedly secured thereto at the lower end thereof a pair of mounting blocks 58 spaced apart longitudinally of the pendulum arms 56. Each of the mounting blocks 58 has a vertical bore therethrough for receiving the lower end of the associated pendulum arm 56, being fixedly secured thereto by a suitable set screw. Each mounting block 58 also has a horizontal bore extending therethrough forwardly of the pendulum arms 56 for receiving the associated end of one of a pair of vertically spaced-apart horizontal cross bars 59, being fixedly secured thereto by suitable set screws. Thus, it will be appreciated that the shaft 36, the pendulum arms 56 and the cross bars 59 cooperate to provide a rigid rectangular pendulum assembly which swings with the rotation of the shaft 36 and is extremely stable and accurate, having negligible sway or wobble.

Mounted on the cross bars 59 is a transducer carriage block 60 which has two horizontal bores therethrough for respectively receiving the cross bars 59 and accommodating sliding movement longitudinally thereof. A set screw 61 is provided for fixing the transducer carriage block 60 to the lower cross bar 59 at any predetermined position therealong. The transducer carriage block 60 also has a vertical bore therethrough slidably receiving therein an elongated support shaft 62 which is provided with an eye bolt 63 in the upper end thereof and is externally threaded at its lower end, as at 64. Another set screw 61a holds the shaft 62 in any desired vertical position. A linear scale 65 is provided on the front surface on the upper one of the cross bars 59, while a linear scale 66 is provided on one side of the vertical shaft 62 for facilitating accurate positioning of the support block 60 along the cross bars 59 and positioning of the shaft 62 with respect to the carriage block 60.

Referring now also to FIGS. 4 and 5, a transducer mounting assembly 70 is carried by the support shaft 62 at its lower end. More specifically, the transducer mounting assembly 70 includes a cylindrical sleeve 71 threadedly engaged with the lower end of the shaft 62 coaxially therewith and projecting therebelow. An annular dial support plate 72, having an annular dial disk 73 on the upper surface thereof, is fixedly secured to the bottom of the sleeve 71 by suitable fasteners, such as screws 74. Extending coaxially into the lower end of the sleeve 71, threadedly engaged therewith and extending therebelow is a stud 76. Received over the lower end of the stud 76 is a cylindrical bearing 75. Fitted telescopically over the bearing 75 is an annular housing plate 77 which extends laterally beyond the outer edges of the dial support plate 72. Washers 78 and a nut 79 cooperate with the stud 76 fixedly to hold the bearing 75 and the housing plate 77 in place.

A lock block 80 overlies the housing plate 77 and is secured thereto by a roll pin 81. The lock block 80 has a disk-engaging lug 82 which extends radially inwardly and overlies the upper surface of the dial disk 73. A clamping screw 83 extends through the lock block 80 and into the housing plate 77 for adjusting the frictional force with which the disk-engaging lug 82 engages the dial disk 73. Thus, it will be appreciated that when the lock block 80 is tightened down in its locking configuration, illustrated in FIG. 5, the dial disk 73 and the housing plate 77 are clamped together so that the housing plate 77 is not movable with respect to the dial support plate 72. The screw 83 is loosened to unlock the lock block 80 and permit the housing plate 77 to be freely rotated about the axis of the stud 76 with respect to the dial disk 73. Mounted on the upper surface of the housing plate 77 is an index plate 84 which cooperates with a dial scale (not shown) on the dial disk 73 accurately to indicate the angular position of the housing plate 77 with respect to the dial disk 73.

A transducer array 85 to be calibrated is fixedly secured to the housing plate 77. More specifically, the transducer array 85 is provided with an annular base plate 86 which is fixedly secured to the underside of the housing plate 77 by suitable fasteners 88 (see FIG. 4). The base plate 86 carries a plurality of ultrasonic transducers 87, including transmitting transducers and receiving transducers, which are oriented in a manner determined by the nature and shape of the particular calibration block 11 to be used in the calibration procedure.

Also mounted on the pendulum carriage assembly 30 adjacent to the drive assembly 40 is a dial assembly 90. More specifically, two elongated support brackets 91 are fixedly secured to the associated clamp bar 31 and depend vertically therefrom. A flat dial plate 92 is fixedly secured to the support brackets 91 outboard thereof by fasteners 93, the dial plate 93 having an arcuate lower edge provided with a scale 94. An elongated pointer 95 has a hub 96 at one end thereof which is fixedly secured to the adjacent end of the shaft 36 for rotation therewith. Thus, it will be appreciated that the pointer 95 indicates on the scale 94 the angular position of the pendulum assembly 50, the pointer 95 being vertical when the pendulum assembly 50 is oriented vertically. Preferably the scale 94 of the dial assembly 90 is calibrated in radians so that the travel distance of the pendulum assembly 50 along its travel arc may be determined by multiplying the angle in radians by the radius of the travel arc.

Fixedly secured to the clamp block 51 adjacent to the drive assembly 40 is an elongated rectangular bias arm 100 which projects rearwardly of the calibration apparatus 10. Fixedly secured to the bias arm 100 adjacent to its distal end, as by a fastener 101, is a bias weight 102. The bias weight 102 serves normally to bias the pendulum assembly 50 to a rest position, indicated in broken line in FIG. 1, wherein the pointer 95 is off the scale 94 which defines the limits of the normal range of operation of the pendulum assembly 50 during the calibration procedure.

The purpose of this bias arrangement is to avoid backlash in the drive assembly 40. More particularly, the gearmotor 42 has a worm gear drive with a high speedreduction ratio, which is characterized by high friction. This is advantageous in that it serves to hold the pendulum assembly 50 in position when power to the motor 42 is shut off. But in this type of drive, each direction change of the gearmotor 42 is attended by backlash in the gear train. This "play" in the gear train effects a jolt at each extremity of the pendulum swing, and introduces a spurious movement into the pendulum assembly 50 which adversely affects the accuracy of the calibration procedure. The bias weight 102, by establishing the normal rest position of the pendulum assembly 50 outside the normal calibration range, insures that the frictional forces on the gear train will always be exerted in the same direction, thereby eliminating the backlash.

In operation, the pendulum assembly 50 is raised to a position where the lower end of the support shaft 62 is well above the calibration tank 13, and the transducer array 85 is mounted in place on the transducer mounting assembly 70. The calibration block 11 is positioned in the calibration tank 13 immediately below the calibration apparatus 10, with the curvature of the arcuate upper surface 12 being oriented in the direction of the swing of the pendulum assembly 50. The pendulum carriage assembly 30 is positioned so that the shaft 36 is disposed coaxially with the axis of curvature of the upper surface 12 of the calibration block 11. The pendulum assembly 50 is then lowered until the transducer array 85 is positioned the predetermined desired distance from the upper surface 12 of the calibration block 11.

It is a significant feature of the present invention that accurate positioning of the transducer array 85 is facilitated by several different degrees of adjustment of the pendulum assembly 50. Thus, the entire pendulum carriage assembly 30 may be moved vertically along the support posts 23. Also, the vertical position of the pendulum assembly 50 may be coarsely adjusted by movement of the pendulum arms 56 vertically with respect to the clamp blocks 51. A finer vertical adjustment may be effected by vertical movement of the support shaft 62 with respect to the transducer carriage block 60. Horizontal positioning of the transducer array 85 is effected by sliding the transducer carriage block 60 horizontally along the cross bars 59.

When the transducer array 85 has been accurately positioned over the calibration block 11, the gearmotor 42 is energized to move the pendulum assembly into the calibration range and swing it back and forth. It will be appreciated that the effective radius of the pendulum assembly 50 is adjusted so that the arc traversed by the transducer array 85 is coaxial with the arcuate upper surface 12 of the calibration block 11, so that the predetermined distance therebetween remains constant.

The calibration block 11 may have a substantial width transversely of the calibration apparatus 10. In order to cover the entire surface 12, it will be necessary to move the transducer array 85 thereacross in sequential parallel passes. Thus, the transducer carriage block 60 may be moved a slight distance horizontally after each pass to place the transducer array 85 in position for the next pass. It will also be appreciated that by rotation of the housing plate 77 of the transducer mounting assembly 70, the angular rotation of the transducer array 85 may also be changed, as desired.

A significant advantage of the present invention is its great stability and accuracy which is afforded by the dual pendulum arms 56 and the dual cross bars 59. This rigid rectangular construction, plus the bias weight 102 which eliminates backlash from the drive assembly 40, serves to provide a smooth and accurately controlled movement of the pendulum assembly 50 at a constant and predictable rate of travel.

From the foregoing, it can be seen that there has been provided an improved calibration apparatus for calibrating ultrasonic transducer arrays, the apparatus being characterized by a simple and economical construction which affords great stability and accuracy of movement of the pendulum assembly, multiple adjustments of the position of the transducer array, including coarse and fine adjustments of the pendulum radius, and scales to indicate all ranges of adjustment and movement.

We claim:

1. Calibration apparatus for calibrating an ultrasonic transducer array by moving it along an arcuate calibration test member, said apparatus comprising: a frame including four upstanding posts in a rectangular arrangement disposable adjacent to the test member, carriage means including a framework extending between and interconnecting said posts and being mounted for sliding vertical movement there along and defining a pivot axis extending through the center of curvature of the test member, means for changing the position of said carriage means on said frame for varying the position of said pivot axis with respect to the test member thereby to accommodate test members with different radii of curvature, an elongated pendulum arm mounted on said carriage and depending therefrom for pivotal movement about said pivot axis, drive means for effecting pivotal movement of said pendulum arm, and attachment means for mounting the transducer array on the lower end of said pendulum arm, whereby pivoting of said pendulum arm effects movement of the transducer array along the arcuate test member at a fixed predetermined distance therefrom.

2. Calibration apparatus for calibrating an array by moving it along an arcuate calibration test member, said apparatus comprising: a frame disposable adjacent to the test member, carriage means mounted on said frame and defining a pivot axis extending through the center of curvature of the test member, means for changing the position of said carriage means on said frame for varying the position of said pivot axis with respect to the test member thereby to accommodate test members with different radii of curvature, an elongated pendulum arm mounted on said carriage and depending therefrom for pivotal movement about said pivot axis, drive means for effecting pivotal movement of said pendulum arm, and attachment means for mounting the transducer array on the lower end of said pendulum arm and for accommodating rotation of the transducer array about an axis parallel to said pendulum arm whereby pivoting of said pendulum arm effects movement of the transducer array along the arcuate test member at a fixed predetermined distance therefrom.

3. The calibration apparatus of claim 2, wherein said attachment means includes first and second coaxial annular members adapted for rotation with respect to each other about said predetermined axis, means attaching one of said annular members to said pendulum arm, means attaching the transducer array to the other of said annular members, and lock means engageable with said annular members for preventing relative rotation thereof.

4. The calibration apparatus of claim 2, wherein said attachment means includes a swivel joint.

5. Calibration apparatus for calibrating an ultrasonic transducer array by moving it along an arcuate calibration test member, said apparatus comprising: a frame disposable adjacent to the test member, carriage means mounted on said frame and defining a pivot axis extending through the center of curvature of the test member, means for changing the position of said carriage means on said frame for varying the position of said pivot axis with respect to the test member thereby to accommodate test members with different radii of curvature, an elongated pendulum arm mounted on said carriage and depending therefrom for pivotal movement about said pivot axis, drive means for effecting pivotal movement of said pendulum arm, and attachment means for mounting the transducer array on the lower end of said pendulum arm, whereby pivoting of said pendulum arm effects movement of the transducer array along the arcuate test member at a fixed predetermined distance therefrom and further including indicator means coupled to said pendulum arm for indicating the direction and extent of the pivoting movement thereof.

6. Calibration apparatus for calibrating an ultrasonic transducer array by moving it along an arcuate calibration test member, said apparatus comprising: a frame disposable adjacent to the test member, carriage means mounted on said frame and defining a pivot axis extending through the center of curvature of the test member, means for changing the position of said carriage means on said frame for varying the position of said pivot axis with respect to the test member thereby to accommodate test members with different radii of curvature, an elongated pendulum arm having a longitudinal axis which does not intersect said pivot axis and mounted on said carriage and depending therefrom for pivotal movement about said pivot axis, drive means for effecting pivotal movement of said pendulum arm, and attachment means for mounting the transducer array on the lower end of said pendulum arm, whereby pivoting of said pendulum arm effects movement of the transducer array along the arcuate test member at a fixed predetermined distance therefrom.

7. Calibration apparatus for calibrating an ultrasonic transducer array by moving it along an arcuate calibration test member, said apparatus comprising: a frame disposable adjacent to the test member, carriage means mounted on said frame and defining a pivot axis extending through the center of curvature of the test member, a pair of parallel pendulum arms mounted on said carriage and depending therefrom for pivotal movement about said pivot axis, support means rigidly interconnecting said pendulum arms adjacent to the lower ends thereof and maintaining said arms parallel to each other, drive means for effecting pivotal movement of said pendulum arms, attachment means for mounting the transducer array on said support means so that pivoting of said pendulum arms effects movement of the transducer array along the arcuate test member at a fixed predetermined distance therefrom, and means for changing the position of said attachment means laterally along said support means for varying the position of the transducer array between said pendulum arms thereby to accommodate lateral positioning of the transducer array with respect to the test member.

8. The calibration apparatus of claim 7, and further including means accommodating adjustment of the position of said attachment means radially of the test member.

9. The calibration apparatus of claim 8, wherein said adjustment means includes means for changing the position of said carriage means on said frame for varying the position of said pivot axis with respect to the test member.

10. The calibration apparatus of claim 8, wherein said adjustment means includes means for varying the position of said attachment means on said support means in directions radially of the test member.

11. The calibration apparatus of claim 7, wherein said support means includes a pair of parallel cross bars extending between said pendulum arms perpendicular thereto.

12. The calibration apparatus of claim 7, wherein said support means includes a cross bar extending between said pendulum arms perpendicular thereto, and a mounting block carried by said cross bar for sliding movement longitudinally thereof.

13. The calibration apparatus of claim 12, wherein said support means further includes an elongated mounting rod carried by said mounting block in a position substantially parallel to said pendulum arms and slidably movable longitudinally with respect to said mounting block.

14. The calibration apparatus of claim 7, wherein said pendulum arms have longitudinal axes which define a plane parallel to and spaced from said pivot axis.

15. Calibration apparatus for calibrating an ultrasonic transducer array by moving it along an arcuate calibration test member, said apparatus comprising: a frame disposable adjacent to the test member, a pivot shaft rotatably mounted on said frame, a reversible speed reduction gearmotor carried by said frame and having an output shaft, chain and sprocket means interconnecting said output shaft and said pivot shaft, an elongated pendulum arm fixedly secured to said pivot shaft and depending therefrom substantially perpendicular thereto for pivoting motion in response to rotation of said pivot shaft, bias means coupled to said pendulum arm for minimizing blacklash in said speed reduction gearmotor, and attachment means for mounting the transducer array on the lower end of said pendulum arm, whereby pivoting of said pendulum arm effects movement of the transducer array along the arcuate test member at a fixed predetermined distance therefrom.

* * * * *